(12) United States Patent
Damrau et al.

(10) Patent No.: US 7,098,354 B2
(45) Date of Patent: Aug. 29, 2006

(54) RACEMOSELECTIVE SYNTHESIS OF RAC-DIORGANOSILYLBIS(2-METHYLBENZO[E]INDEYL)ZIRCONIUM COMPOUNDS

(75) Inventors: Hans-Robert Damrau, Constance (DE); Patrik Müller, Frankfurt (DE); Valerie Garcia, Compiègne (FR); Christian Sidot, Compiègne (FR); Christian Tellier, Compiègne (FR); Jean-Francois Lelong, Tracy-le-Mont (FR)

(73) Assignee: Basell Polyolefine GmbH, Frankfurt am Main (DE)

( * ) Notice: Subject to any disclaimer, the term of this patent is extended or adjusted under 35 U.S.C. 154(b) by 98 days.

(21) Appl. No.: 10/532,511

(22) PCT Filed: Oct. 22, 2003

(86) PCT No.: PCT/EP03/11681

§ 371 (c)(1),
(2), (4) Date: Apr. 25, 2005

(87) PCT Pub. No.: WO2004/037840

PCT Pub. Date: May 6, 2004

(65) Prior Publication Data

US 2006/0167295 A1 Jul. 27, 2006

Related U.S. Application Data

(60) Provisional application No. 60/431,805, filed on Dec. 9, 2002.

(30) Foreign Application Priority Data

Oct. 25, 2002 (DE) ................ 102 50 060

(51) Int. Cl.
*C07F 17/00* (2006.01)
*B01J 31/00* (2006.01)

(52) U.S. Cl. .............. 556/11; 556/12; 526/160; 526/943; 502/103; 502/117

(58) Field of Classification Search .......... 556/11, 556/12; 526/160, 943; 502/103, 117
See application file for complete search history.

(56) References Cited

U.S. PATENT DOCUMENTS 5,830,821 A * 11/1998 Rohrmann et al. ........ 502/117

| 6,262,286 B1 | 7/2001 | Gregorius et al. |
| 6,620,953 B1 | 9/2003 | Bingel et al. |
| 2004/0010157 A1 | 1/2004 | Damrau et al. |

FOREIGN PATENT DOCUMENTS

| DE | 100 30 638 | 1/2002 |
| EP | 0 700 935 | 3/1996 |
| EP | 0 834 514 | 4/1998 |
| WO | WO-99/15538 | 4/1999 |
| WO | WO-00/31089 | 6/2000 |
| WO | WO-00/31090 | 6/2000 |
| WO | WO-00/31091 | 6/2000 |
| WO | WO-02/00672 | 1/2002 |

OTHER PUBLICATIONS

Damrau et al., Racemo-Selective Synthesis of ansa-Zricocene Derivates from Zirconium Biphenolate Complexes, Nov. 8, 2001, Organometallics, vol. 20, No. 25, pp. 5258-5265.*
Rheingold, A. L. et al., "Preparation and Properties of Chiral Titanocene and Zirconocene Dichloride Complexes of a Chrial Ligand", Organometallics (1992), vol. 11, pp. 1869-1876.

* cited by examiner

*Primary Examiner*—Porfirio Nazario-Gonzalez
(74) *Attorney, Agent, or Firm*—Connolly Bove Lodge & Hutz LLP

(57) ABSTRACT

The present invention relates to a specific process for the diastereoselective synthesis of rac-diorganosilylbis(2-methylbenzo[e]indenyl)zirconium compounds of the formula I,

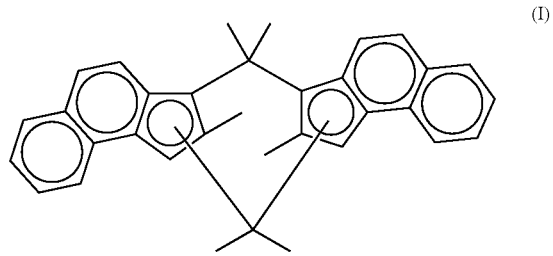

(I)

by reacting the silyl-bridged bisindenyl ligand with a dihalozirconium bis(3,5-di-tert-butylphenoxide)-base adduct to form the diorganosilylbis(2-methylbenzo[e]indenyl)zirconium bis(3,5-di-tert-butylphenoxide) and subsequently replacing the phenoxide groups by X using suitable replacement reagents to give the compound of the formula I; where the substituents X can be identical or different and are each F, Cl, Br, I or linear, cyclic or branched $C_{1-10}$-alkyl; and the substituents R can be identical or different and are each linear, cyclic or branched $C_{1-10}$-alkyl or $C_{6-10}$-aryl; and also to the use of these compounds as catalysts.

18 Claims, No Drawings

RACEMOSELECTIVE SYNTHESIS OF RAC-DIORGANOSILYLBIS(2-METHYLBENZO[E]INDEYL)ZIRCONIUM COMPOUNDS

This application is a national stage application (under 35 U.S.C. 371) of PCT/EP2003/011681 filed Oct. 22, 2003 which claims benefit to German application 102 50 060.6 filed Oct. 25, 2002 and U.S. provisional application 60/431,805 filed Dec. 9, 2002.

The present invention relates to a process for the racemoselective synthesis of rac-diorganosilylbis(2-methylbenzo[e]indenyl)zirconium compounds and especially for the racemoselective synthesis of rac-dimethylsilylbis(2-methylbenzo[e]indenyl)zirconium dichloride. In particular, the present invention relates to a process for the racemoselective synthesis of the abovementioned compound via the racemoselective synthesis of dimethylsilylbis(2-methylbenzo[e]indenyl)zirconium bis(3,5-di-tert-butylphenoxide).

Chiral metallocene complexes of metals of transition groups three to six of the Periodic Table of the Elements are increasingly being used for stereospecific olefin polymerization. Appropriately substituted ansa-metallocene complexes are generally obtained as a diastereomer mixture consisting of the racemic form and the meso form of the metallocene from processes of the prior art. Stereospecific olefin polymerization generally requires the use of the metallocene complex in its racemic form, i.e. without the mirror-symmetric meso compounds. For this reason, in the metallocene synthesis according to the prior art, the meso form has to be separated off from the diastereomer mixture.

Since the meso form is usually not able to be isomerized, this form has to be destroyed or removed after the synthesis, so that the yield of racemic metallocene complexes is low in syntheses according to the prior art.

WO 99/15538 and DE 100 30 638 describe a general, multistage process for preparing racemic metal complexes via biphenoxide- or bisphenoxide-substituted metallocenes as intermediates.

The synthesis of ansa-zirconocene dichloride complexes according to the prior art is generally carried out by a general route starting from $ZrCl_4$ or its solvent adducts. The cyclopentadienyl ligand is usually dissolved or suspended in toluene, with or without addition of small amounts of THF or DME, deprotonated by means of strong bases and subsequently reacted with zirconium tetrachloride in order to obtain the corresponding ansa-metallocene dichlorides and two equivalents of alkali metal chloride/alkaline earth metal chloride. The ansa-metallocene dichloride is separated from the alkali metal or alkaline earth metal salts by means of filtration and is isolated by crystallization.

This classical reaction path has two substantial problems. In place of the desired racemate, virtually equivalent amounts of the mirror-symmetric meso diastereomer are formed in most cases. Furthermore, the yields of the rac/meso mixture in this process are relatively low and are in the range from about 30 to 40%. Since, as mentioned above, only the racemate form can be used for the catalytic applications of ansa-metallocene compounds, the synthesis of the rac/meso mixture of the ansa-metallocene compounds has to be followed by either a complicated separation of diastereomers or destruction of the meso form, which again approximately halves the yield. The total yield of pure rac-ansa-metallocene is therefore generally not more than 15–20%.

A further disadvantage is the efficiency of the synthetic route. As described above, the ansa-metallocene compound has to be separated off from the alkali metal halides or alkaline earth metal halides formed as coproducts, and in some cases this proves to be difficult because of the low solubility of the ansa-metallocene compound, in particular in toluene, since the alkali metal halides or alkaline earth metal halides are also virtually insoluble in organic solvents. This separation step therefore requires large amounts of solvent, which in turn has an adverse effect on the productivity and effectiveness of the synthetic route.

It is an object of the present invention to find a process for the selective preparation of racemic metallocene complexes which are virtually free of the meso isomer.

We have found that this object is achieved by the process claimed in the independent process claim. Preferred embodiments of the present invention are obtained by combining the features of the main claim with the features of the dependent, subordinate claims.

The present invention provides a specific process for the diastereoselective synthesis of rac-diorganosilylbis(2-methylbenzo[e]indenyl)zirconium compounds of the formula I,

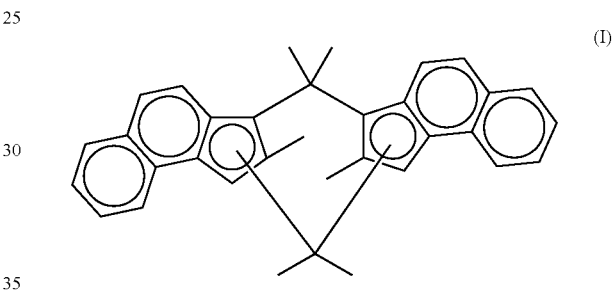

which comprises the following steps:

a) reaction of a compound of the formula II with a zirconium bisphenoxide complex of the formula III to form the ansa-zirconocene bisphenoxide complex of the formula IV,

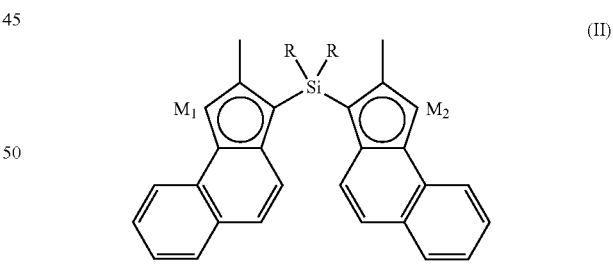

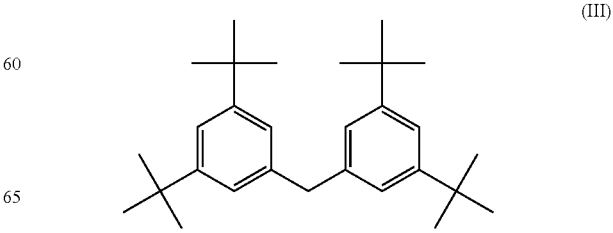

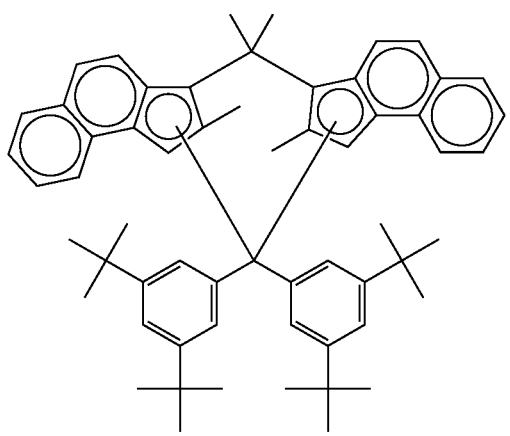

(IV)

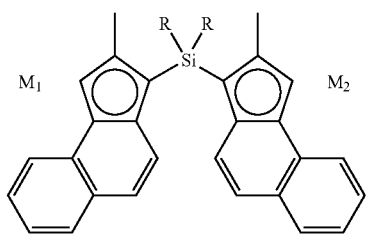

(II)

where $M_1$ and $M_2$ are monovalent positive alkali metal ions or $M_1$ and $M_2$ together represent a divalent positive alkaline earth metal ion;

c) reaction of the compound of the formula II with a zirconium bisphenoxide complex of the formula III:

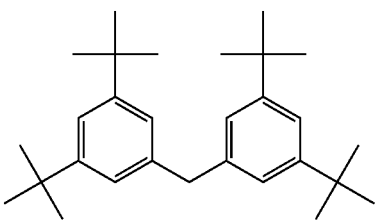

(III)

where LB is a suitable Lewis base, to give a compound of the formula IV:

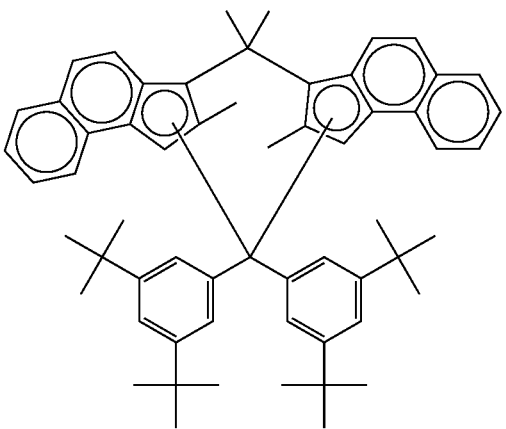

(IV)

b) replacement of the phenoxide groups of IV by X using suitable replacement reagents to give the compound of the formula I;

where the substituents X can be identical or different and are each F, Cl, Br, I, or linear, cyclic or branched $C_{1-10}$-alkyl; and the substituents R can be identical or different and are each linear, cyclic or branched $C_{1-10}$-alkyl or $C_{6-10}$-aryl; and LB is a suitable Lewis base, and $M_1$ and $M_2$ are monovalent positive alkali metal ions or $M_1$ and $M_2$ together represent a divalent positive alkaline earth metal ion.

A particularly preferred embodiment of the process of the present invention for the diastereoselective synthesis of rac-diorganosilylbis(2-methylbenzo[e]indenyl)zirconium compounds of the formula I,

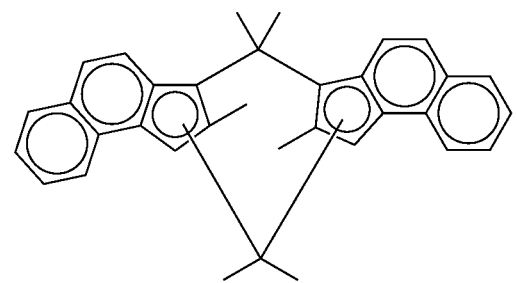

(I)

comprises the following steps:

a) deprotonation of 2-methylbenzo[e]indene by means of a suitable deprotonating agent;

b) reaction of the deprotonated 2-methylbenzo[e]indene with a diorganosilyl compound $R_2SiY_2$, where the substituents R can be identical or different and are each linear, cyclic or branched $C_{1-10}$-alkyl or $C_{6-10}$-aryl and the leaving groups Y can be identical or different and are each F, Cl, Br or I, and subsequent repeat deprotonation by means of a suitable deprotonating agent, giving a compound of the formula II:

d) reaction of the compound of the formula IV with suitable replacement reagents so as to replace the phenoxide groups of IV by X to give the compound of the formula I, where the substituents X can be identical or different and are each F, Cl, Br, I or linear, cyclic or branched $C_{1-10}$-alkyl.

The process of the present invention is particularly preferably carried out with the intermediate IV being converted in the same reaction vessel in which it has been formed into the complex I by replacement of the phenoxide groups.

Furthermore, preference is given, according to the present invention, to the substituents R being selected from among methyl, ethyl, n-propyl, isopropyl, n-butyl, isobutyl and phenyl and combinations thereof. The substituents X are preferably selected from among F, Cl, Br, I, methyl, ethyl, n-propyl, isopropyl, n-butyl and isobutyl, more preferably Cl and/or methyl. Preference is also given to $M_1$ and $M_2$ being selected from among lithium, sodium, potassium, rubidium or cesium ions or together representing magnesium. Particular preference is given to R being methyl or ethyl, X being Cl and LB being THF or DME, and $M_1$ and $M_2$ each being Li. The Lewis base LB used is preferably tetrahydrofuran (THF), dimethoxyethane (DME) or tetramethylethanediamine (TMEDA).

In the process of the present invention, a Lewis base, preferably THF or DME, may, if appropriate, be added once again in the replacement of the phenoxide groups of the complex IV.

The terms "meso form", "racemate" and thus also "diastereomers" and "enantiomers" are known in the context of metallocene complexes and are defined, for example, in Reingold et al., Organometallics 11 (1992), pages 1869–1876. For the purposes of the present invention, the term "virtually meso-free" or "racemoselective" means that more than 80%, preferably at least 90%, of a compound are present in the form of the racemate, particularly preferably at least 95%.

We have surprisingly found, according to the present invention, that diorganosilylbis(2-methylbenzo[e]indenyl) zirconocene compounds I can be obtained racemoselectively in a simple manner via the corresponding diorganosilylbis (2-methylbenzo[e]indenyl)zirconium bis(3,5-di-tert-butylphenoxide) IV. Here, use is made of the fact that the reaction of the diorganosilylbis(2-methylbenzo[e]indenyl) metal salt with zirconium bis(3,5-di-tert-butylphenoxide) compounds leads diastereoselectively to a high excess of the racemate form of the complex IV.

It has also been found that the process of the present invention can be carried out without isolation of the intermediates, in a "single-vessel process", starting from 2-methylbenzo[e]indene, with the process proceeding racemoselectively in high total yields. Particular preference is therefore given to the process of the present invention starting from 2-methylbenzo[e]indene being carried out without isolation of intermediates after the individual process steps.

The diastereoselectivity of the synthesis according to the present invention using this ligand system appears, without being tied to a theory, to be based on the space occupied by the tert-butyl substituents in positions three and five of the phenoxide.

Compared to the processes of the prior art, the synthesis strategy according to the present invention leads to significantly improved total yields of the racemate form of the resulting metallocene. Furthermore, the complex IV obtained as intermediate can readily be separated from the alkali metal salts or alkaline earth metal salts formed in parallel because of its good solubility in aliphatic and aromatic solvents. The good solubility of the complex IV additionally makes it possible for the synthesis to be carried out in high concentrations, which leads to increased productivity of the synthetic process of the present invention. In a preferred embodiment, the process is carried out with the complex IV being present in a concentration of 5–30% by weight, preferably 10–25% by weight, particularly preferably 15–25% by weight and very particularly preferably about 20% by weight, based on solvent used.

The metallocene complexes I obtained according to the present invention generally still contain from 1 to 4 equivalents of a Lewis base which are generally introduced via the synthesis. Examples of such Lewis bases are ethers such as diethyl ether or tetrahydrofuran (THF) and amines such as TMEDA. However, it is also possible to obtain the metallocene complexes I free of Lewis bases, for example by drying under reduced pressure or by choice of other solvents in the synthesis. Such measures are known to those skilled in the art.

In the process of the present invention, the silyl-bridged alkali metal or alkaline earth metal bis(benzo[e]indenyl) salt II is reacted with the zirconium bis-(3,5-di-tert-butylphenoxide)-base adduct III to form the metallocene complex IV.

The ligand salts II can be obtained by methods known from the literature using suitable deprotonating agents, for example by the, preferably, stoichiometric, reaction of an organometallic compound or a hydride of an alkali metal or alkaline earth metal with 2-methylbenzo[e]indene.

Suitable organometallic compounds for deprotonating the methylbenzo[e]indene include strong bases, for example n-butyllithium, tert-butyllithium, sodium hydride, potassium tert-butoxide, Grignard reagents of magnesium or suitable compounds of magnesium such as di-n-butylmagnesium or (n,s)-dibutylmagnesium or other suitable alkali metal alkyl or alkaline earth metal alkyl compounds.

Two mol of the deprotonated indene are subsequently reacted with diorganosilane dihalogen compounds of the formula $R_2SiY_2$, where the substituents R can be identical or different and are each linear, cyclic or branched $C_{1-10}$-alkyl or $C_{6-10}$-aryl and the leaving groups Y can be identical or different and are each F, Cl, Br or I.

Preferred compounds $R_2SiY_2$ are dialkylsilane dichlorides such as dimethylsilane dichloride, diethylsilane dichloride or dipropylsilane dichloride, or else diarylsilane dichlorides such as diphenylsilane dichloride or alkylarylsilane dichlorides such as phenylmethylsilane dichloride.

The reaction products obtained are then once again deprotonated using the deprotonating agents as mentioned above to form the ansa-ligand salt II.

Selected examples of compounds of the formula II which can be used according to the present invention are:
dimethylsilanediylbis(2-methylbenzo[e]indenyl)dilithium
diethylsilanediylbis(2-methylbenzo[e]indenyl)dilithium
diphenylsilanediylbis(2-methylbenzo[e]indenyl)dilithium
phenylmethylsilanediylbis(2-methylbenzo[e]indenyl)dilithium
dimethylsilanediylbis(2-methylbenzo[e]indenyl)magnesium
diethylsilanediylbis(2-methylbenzo[e]indenyl)magnesium
diphenylsilanediylbis(2-methylbenzo[e]indenyl)magnesium
phenylmethylsilanediylbis(2-methylbenzo[e]indenyl)magnesium and also the respective Lewis base adducts of these compounds with, for example, THF, DME or TMEDA.

In parallel, two equivalents of 3,5-di-tert-butylphenol are likewise deprotonated by means of suitable strong bases as mentioned above in a manner known from the literature, preferably by means of butyllithium or Grignard compounds or other alkyllithium compounds, and subsequently reacted with zirconium tetrachloride or other zirconium halides such as zirconium tetrafluoride, tetrabromide or tetraiodide in suitable solvents, in the presence or absence of suitable Lewis bases, to form the zirconium bisphenoxide compound III.

Suitable solvents for this purpose are aliphatic hydrocarbons such as pentane, hexane, heptane, aromatic hydrocarbons such as toluene, ortho-, meta- or para-xylene or isopropylbenzene (cumene), and also ethers, such as tetrahydrofuran (THF), diethyl ether, methyl tert-butyl ether or dimethoxyethane (DME), amines such as diisopropylamine, tetramethylethanediamine (TMEDA) or pyridine, with the latter also being suitable Lewis bases.

Suitable Lewis bases for stabilizing the zirconium bisphenoxide complexes (III) in the form of the Lewis base adduct are, for example, THF, 1,2-dimethoxyethane (DME), TMEDA, ethers, amines, cyclic ethers, pyridine and the like. All Lewis bases which lead to adduct formation with the zirconium complexes are suitable for the purposes of the present invention.

Solvent mixtures or solvent/Lewis base mixtures which are well suited to the synthesis of III are mixtures of toluene and THF, toluene and DME or toluene and TMEDA, with the Lewis base generally being present in an amount of from 0.1 to 50 mol %, preferably from 1 to 20 mol %, based on the solvent mixture.

The reaction of the ligand salt II with the zirconium bis(3,5-di-tert-butylphenoxide)-base adduct III to form the ansa-metallocene complex IV usually takes place in an organic solvent or suspension medium, preferably a solvent mixture comprising a Lewis-basic solvent, in the temperature range from −78° C. to 250° C., preferably from 0 to 110° C. Well suited solvents are aliphatic hydrocarbons such as pentane, hexane, heptane, aromatic hydrocarbons such as toluene, ortho-, meta- or para-xylene or isopropylbenzene (cumene), ethers, such as tetrahydrofuran (THF), diethyl ether, methyl tert-butyl ether or dimethoxyethane (DME), amines such as diisopropylamine, tetramethylethanediamine (TMEDA) or pyridine. Well suited solvent mixtures are mixtures of toluene and THF, toluene and DME or toluene and TMEDA, with the Lewis base generally being present in an amount of from 0.1 to 50 mol %, preferably from 1 to 20 mol %, based on the solvent mixture. The molar ratio of the complex III to the alkali metal or alkaline earth metal ligand salt II is usually in the range from 0.8:1 to 1:1.2, preferably 1:1.

The reaction according to the present invention of the ligand salt II with the zirconium bisphenoxide complex III gives the corresponding diorganosilyl bis(2-methylbenzo[e]-indenyl)zirconium bisphenoxide complex IV racemoselectively, with the rac:meso ratio for this compound being at least 4:1, preferably about 5:1, and particularly preferably 6–10:1. Under appropriate reaction conditions, rac/meso ratios of 11:1 and more can also be obtained.

In the final synthesis step, the phenoxide groups are split off, preferably at room temperature, by means of a suitable "replacement agent", in particularly preferred embodiments by means of acetyl chloride or ethylaluminum dichloride, so as to give the racemic metal complex I. It has been found that, in general, no isomerization of the complex takes place during this replacement step.

The phenoxide groups of the racemic complex IV can be completely split off or replaced in a simple manner essentially without rac/meso isomerization and can, if appropriate, be reused.

Suitable replacement (substitution) methods are reaction of the racemic metallocene complexes of the formula IV with appropriate replacement reagents such as $SOCl_2$, silicon tetrachloride, methylaluminum dichloride, dimethylaluminum chloride, aluminum trichloride, dialkylaluminum chlorides, aluminum sesquichlorides, particularly preferably ethylaluminum dichloride, or else inorganic Brönsted acids such as hydrogen halides, i.e. HF, HBr, HI, preferably HCl, which are generally employed as such or as a solution in water or organic solvents such as diethyl ether, THF. Well suited solvents for this purpose are aliphatic hydrocarbons such as pentane, hexane, heptane, aromatic hydrocarbons such as toluene, ortho-, meta- or para-xylene or isopropylbenzene (cumene), ethers such as tetrahydrofuran (THF), diethyl ether, methyl tert-butyl ether or dimethoxyethane (DME), amines such as diisopropylamine, tetramethylethanediamine (TMEDA) or pyridine. Very well suited solvents also include Lewis base-containing solvent mixtures of hydrocarbons and ethers or amines or both, for example mixtures of toluene and THF, toluene and DME or toluene and TMEDA, with the Lewis base generally being present in an amount of 0.01–50 mol %, preferably 0.1–10 mol %, based on the solvent mixture.

Further particularly well suited replacement reagents are aliphatic and aromatic carboxylic acid halides such as acetyl chloride, phenylacetyl chloride, 2-thiophenacetyl chloride, trichloroacetyl chloride, trimethylacetyl chloride, O-acetylmandelyl chloride, 1,3,5-benzenetricarboxylic chloride, 2,6-pyridinecarboxylic chloride, tert-butylacetyl chloride, chloroacetyl chloride, 4-chlorobenzacetyl chloride, dichloroacetyl chloride, 3-methoxyphenylacetyl chloride, acetyl bromide, bromoacetyl bromide, acetyl fluoride, benzoyl fluoride, with these generally being used in the above-mentioned solvents or else as such. This substitution reaction usually gives the dihalide analogous to the compound of the formula IV (X=F, Cl, Br, I).

A further well suited substitution method is reaction of the racemic metallocene complexes, preferably those of the formula IV, with organoaluminum compounds such as tri-$C_1$–$C_{10}$-alkylaluminum, i.e. trimethylaluminum, triethylaluminum, tri-n-butylaluminum, tri-isobutylaluminum, as replacement reagent. According to the present state of knowledge, this generally gives the organo compound analogous to the compound IV (X=organic radical, e.g. $C_{1-10}$-alkyl such as methyl, ethyl, n-butyl, i-butyl).

In the replacement reactions, the components are usually used in the stoichiometric ratio, but an excess of replacement reagent can also be used if desired.

The replacement reactions generally take place with retention of the stereochemistry of the metallocene complexes, i.e., in particular, essentially no conversion of the racemic form into the meso form of the metallocene complexes takes place. Rather, in many cases, particularly when using the above-described chlorination methods, the rac selectivity can be additionally increased while generally retaining the stereochemistry of the starting bisphenoxide complexes IV.

Particularly preferred replacement agents according to the present invention are acetyl chloride, ethylaluminum dichloride and $MeAlCl_2$.

The substitution products formed are relatively easy to separate off from the target complex I since the diorganosilyl (2-methylbenzo[e]indenyl)zirconium compounds formed are generally relatively sparingly soluble and precipitate from the solvent during the replacement reaction. They can therefore be isolated in pure form by filtration and appropriate washing procedures.

Both the 3,5-di-tert-butylphenol used as auxiliary ligand and the replacement or substitution agents used can generally be recovered in a simple manner and can, if appropriate, be recirculated and reused in a similar synthesis process. Furthermore, the auxiliary ligands and replacement agents used are nontoxic and nonmutagenic substances which can be handled without problems and which make the process of the present invention unproblematical in terms of safety requirements.

The process of the present invention makes it possible to obtain the rac form of the metallocene complexes of the formula I very selectively.

The following rac-metallocene compounds of the formula I are particularly preferably obtained by the process of the present invention:

dimethylsilylbis(2-methylbenzo[e]indenyl)zirconium dichloride diethylsilylbis(2-methylbenzo[e]indenyl)zirconium dichloride diphenylsilylbis(2-methylbenzo[e]indenyl)zirconium dichloride phenylmethylsilylbis(2-methylbenzo[e]indenyl)zirconium dichloride phenylethylsilylbis(2-methylbenzo[e]indenyl)zirconium dichloride.

If the replacement step is omitted, the process of the present invention can also be used to obtain the racemic transition metal compound of the formula IV,

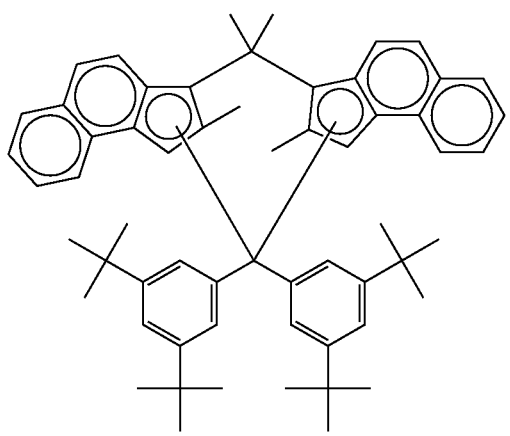
(IV)

where the substituents R can be identical or different and are each linear, cyclic or branched $C_{1-10}$-alkyl or $C_{6-10}$-aryl and are preferably selected from among methyl, ethyl, n-propyl, isopropyl, n-butyl, isobutyl and phenyl and combinations thereof.

The racemic complexes I obtained according to the present invention, like those of the formula IV, can be used as catalysts or in catalyst systems for the polymerization and copolymerization of olefinically unsaturated compounds such as ethylene, propylene, 1-butene, 1-hexene, 1-octene, styrene. They can be used particularly advantageously in the stereoselective polymerization of prochiral, olefinically unsaturated compounds such as propylene and styrene. Suitable catalysts or catalyst systems in which the racemic metallocene complexes according to the present invention can function as "metallocene component" are usually obtained by means of compounds which form metallocenium ions, as described, for example, in EP-A-0 700 935, page 7, line 34, to page 8, line 21, and the formulae (IV) and (V). Further compounds capable of forming metallocenium ions are aluminoxanes $(RAlO)_n$ such as methylaluminoxane, and also boron activators.

The racemic metallocene complexes of the formulae I and IV according to the present invention can also be used as reagents or as catalysts or in catalyst systems in stereoselective, in particular organic, synthesis. Examples which may be mentioned are stereoselective reductions or stereoselective alkylations of C═C double bonds or C═O, C═N double bonds.

In the process of the present invention, the resulting complexes I and IV are obtained in a yield of about 30–80% of rac based on indene compound used.

A further significant advantage is that the process of the present invention can be carried out racemoselectively in a single-vessel process. For the present purposes, a single-vessel process is one in which no intermediates are isolated after the individual process steps. The further reaction can be carried out directly using the reaction product mixtures from the preceding step.

In particular, the intermediate compound IV formed can subsequently be converted into the target compound I by replacement of the phenoxide radicals in a further process step in the same reaction vessel.

The present invention is illustrated by the following specific examples.

EXAMPLE 1

Preparation of dimethylsilylbis(2-methylbenzo[e]indenyl)zirconium bis(3,5-di-tert-butylphenoxide) (IV)

a) Preparation of $ZrCl_4(THF)_2$

In a dry 500 ml three-necked flask which had been flushed with inert gas and was provided with magnetic stirrer bar, dropping funnel and vacuum pump connection with stopcock, 6.4 g (27.46 mmol) of $ZrCl_4$ were suspended in 100 ml of toluene. The suspension was cooled to about 4° C. in an ice bath. 4.5 g of THF were slowly added via the dropping funnel over a period of 15 minutes. The mixture was subsequently allowed to warm to room temperature and was stirred for about 1 hour.

b) Preparation of $Li(3,5-(t-Bu)_2—C_6H_2O)$

In a dry 500 ml three-necked flask provided with magnetic stirrer bar, dropping funnel and vacuum pump connection with stopcock, 11.33 g (54.91 mmol) of 3,5-di-tert-butylphenol were dissolved in 120 ml of toluene and 4.5 g of THF under inert gas. The colorless solution was cooled to 4° C. in an ice bath, and 21.5 ml of a 2.5 molar solution of BuLi in toluene (20% by weight) were then slowly added via the dropping funnel over a period of one hour. The suspension formed was allowed to warm to room temperature and was stirred at room temperature for 1.5 hours.

c) Preparation of $Cl_2Zr(3,5-(t-Bu)_2—C_6H_3O)_2(THF)_2$

The suspension from step b) was introduced under nitrogen by means of a syringe into the suspension from step a) at room temperature over a period of several minutes. Residues of lithium phenoxide were rinsed in using 10 ml of toluene. The resulting suspension was stirred at room temperature for another 4 hours.

d) Preparation of $Me_2Si(2-Me-benzo[e]ind)_2Li_2$

In a dry 1000 ml three-necked flask provided with magnetic stirrer bar, dropping funnel and vacuum connection with stopcock, 11.0 g (26.40 mmol) of $Me_2Si(2-Me-benzo[e]ind)_2$ were suspended in 120 ml of toluene and 6 g of THF under inert gas. 20.5 ml of a 2.6 molar solution of BuLi in toluene were added dropwise to the suspension at room temperature. The resulting suspension was heated to 80° C. and stirred at this temperature for 2 hours.

e) Preparation of $Me_2Si(2-Me-benzo[e]ind)_2Zr(3,5-(t-Bu)_2—C_6H_3O)_2$ (IV)

The suspension from step c) was introduced under nitrogen via a syringe into the suspension from step d). Residues of the zirconium bisphenoxide-THF adduct were washed out using 10 ml of toluene and added. The resulting suspension was stirred at room temperature for 12 hours. A $^1$H-NMR spectrum of the reaction mixture showed the formation of complex IV with a rac/meso ratio of about 5:1. The suspension was heated to 85° C. and stirred for a further 4.5 hours, then cooled to room temperature. The $^1$H-NMR spectrum showed no change in the rac/meso ratio. The suspension was again heated to 85° C. and filtered at this temperature under nitrogen via a glass frit with the aid of a syringe. The filtrate was concentrated to a small volume under reduced pressure and subsequently allowed to stand at room temperature. The complex IV precipitated as a fine powder after a number of hours. The precipitate was filtered off and dried under reduced pressure, giving 14.7 g of the complex IV with a rac/meso ratio of about 8:1 (determined by means of $^1$H-NMR). Yield: 61% (14.7 g).

Recrystallization of the complex IV from toluene gave the complex in pure rac form.

EXAMPLE 2

Preparation of rac-dimethylsilylbis(2-methylbenzo[e]indenyl)zirconium dichloride (I)

3.4 g of rac-dimethylsilylbis(2-methylbenzo[e]indenyl)zirconium bis(3,5-di-tert-butylphenoxide) (IV) from example 1 were suspended in 35.8 g of toluene in a dry round-bottomed flask which had been flushed with inert gas and was provided with stopcock and magnetic stirrer bar. At room temperature, 7.5 g of a 10% strength by weight solution of acetyl chloride in toluene were quickly added to this suspension via a dropping funnel. The mixture was stirred at room temperature. After 4 hours, the reaction mixture was filtered through a glass filter frit number 3 under inert gas. The filter cake was washed twice with 10 g of heptane and subsequently dried under reduced pressure. This gave 1.7 g of the compound I as a yellowish powder. The $^1$H-NMR spectrum of the compound indicated the pure rac form.

| Elemental analysis: | C % (calculated) | 62.48 | C % (found) | 61.9 |
|---|---|---|---|---|
| | H % (calculated) | 4.54 | H % (found) | 4.6 |
| | Cl % (calculated) | 12.29 | Cl % (found) | 12.2 |
| | Zr % (calculated) | 15.82 | Zr % (found) | 15.8 |

EXAMPLE 3

Preparation of rac-dimethylsilylbis(2-methylbenzo[e]indenyl)zirconium dichloride (I) by splitting off the phenoxides from IV using 2.5 equivalents of acetyl chloride and one equivalent of THF In a dry round-bottomed flask which had been flushed with inert gas and was provided with stopcock and magnetic stirrer bar, 3.4 g (3.71 mmol) of the complex IV from example 1 were suspended in 33.6 g of toluene and 0.7 g of THF. At room temperature, 7.3 g of a 10% strength by weight solution of acetyl chloride in toluene (9.30 mmol) were added quickly to this suspension via a dropping funnel. The mixture was stirred at room temperature. After 4.5 hours, the reaction mixture was filtered through a glass filter frit number 3 which was flushed with inert gas. The filter cake was washed twice with 10 g of heptane and dried under reduced pressure. This gave 1.9 g of the compound I as a yellow powder. The $^1$H-NMR spectrum showed the presence of the pure rac form of I.

| Elemental analysis: | C % (calculated) | 62.48 | C % (found) | 62.6 |
|---|---|---|---|---|
| | H % (calculated) | 4.54 | H % (found) | 4.6 |
| | Cl % (calculated) | 12.29 | Cl % (found) | 12.2 |
| | Zr % (calculated) | 15.82 | Zr % (found) | 16.0 |

EXAMPLE 4

Preparation of rac-dimethylsilylbis(2-methylbenzo[e]indenyl)zirconium dichloride (I) by splitting off the phenoxides from dimethylsilylbis(2-methylbenzo[e]indenyl)zirconium bis(3,5-di-tert-butylphenoxide) (IV) using 2.6 equivalents of acetyl chloride and two equivalents of DME 4.1 g of the complex IV (4.47 mmol) from example 1 were suspended in 40.6 g of toluene and 0.9 g (9.98 mmol) of DME in a dry round-bottomed flask which had been flushed with inert gas and was provided with stopcock and magnetic stirrer bar. At room temperature, 9.1 g (11.59 mmol) of a 10% strength by weight solution of acetyl chloride in toluene were added quickly to this suspension via a dropping funnel. The reaction mixture was stirred at room temperature. After 4.5 hours, the reaction mixture was filtered by means of a glass filter frit number 4 which was flushed with inert gas. The filter cake was washed twice with 10 g of heptane and subsequently dried under reduced pressure. This gave 2.1 g of the compound I as a yellow powder. The $^1$H-NMR spectrum indicated the presence of the pure rac form.

| Elemental analysis: | C % (calculated) | 62.48 | C % (found) | 62.8 |
|---|---|---|---|---|
| | H % (calculated) | 4.54 | H % (found) | 4.6 |
| | Cl % (calculated) | 12.29 | Cl % (found) | 12.3 |
| | Zr % (calculated) | 15.82 | Zr % (found) | 15.7 |

EXAMPLE 5

Preparation of rac-dimethylsilylbis(2-methylbenzo[e]indenyl)zirconium dichloride (I) via racemoselective synthesis of dimethylsilylbis(2-methylbenzo[e]indenyl)zirconium bis(3,5-di-tert-butylphenoxide) (IV) using THF as Lewis base a) Preparation of ZrCl$_4$(THF)$_2$ In a dry 500 ml round-bottomed flask which had been flushed with inert gas and was provided with stopcock and magnetic stirrer bar and also a dropping funnel, 10.0 g (42.91 mmol) of ZrCl$_4$ were suspended in 130 g of toluene. The suspension was cooled to about 4° C. in an ice bath. 3.10 g of THF in 38 g of toluene were then slowly added dropwise via the dropping funnel over a period of 15 minutes. The resulting suspension was allowed to warm to room temperature and was stirred for one hour.

b) Preparation of Li(3,5-(t-Bu)$_2$—C$_6$H$_2$O)

In a dry 500 ml round-bottomed flask which had been flushed with inert gas and was provided with stopcock and magnetic stirrer bar and also a dropping funnel 17.9 g (86.75 mmol) of 3,5-di-tert-butylphenol were dissolved in 130 g of toluene and 6.4 g of THF. The solution was cooled to about 4° C. in an ice bath and 29.0 g of a 20% strength by weight BuLi solution were subsequently added via the dropping funnel over a period of 10 minutes. After the addition was complete, the reaction mixture was allowed to warm to room temperature and was stirred for a further period of about one hour.

c) Preparation of $Cl_2Zr(3,5-(t-Bu)_2—C_6H_3O)_2(THF)_2$

The suspension from step b) was transferred under nitrogen by means of a syringe into the suspension from step a) at room temperature over a period of several minutes. The suspension was stirred at room temperature for a further 2.5 hours.

d) Preparation of $Me_2Si(2-Me-benzo[e]ind)_2Li_2$

In a dry 1 000 ml three-necked round-bottomed flask which had been flushed with inert gas and was provided with magnetic stirrer bar, dropping funnel and vacuum connection with stopcock, 16.7 g (40.08 mmol) of the ligand $Me_2Si(1-H-2-Me-benz[e]indenyl)_2$ were suspended in 157 g of toluene and 6.1 g of THF. 27.1 g of a 20% strength by weight BuLi solution were slowly added dropwise at room temperature to the suspension over a period of 10 minutes. The reaction mixture was heated to 80° C. and stirred at this temperature for 2 hours. It was subsequently cooled to room temperature.

e) Preparation of Complex IV

The suspension from step c) was transferred under nitrogen by means of a syringe into the suspension from step d) at room temperature over a period of 5 minutes. The suspension was stirred at room temperature for 12 hours. The $^1$H-NMR spectrum of the reaction mixture showed that the complex IV had been formed with a rac/meso ratio of about 5:1. The suspension was transferred at room temperature under nitrogen by means of a syringe to a glass filter frit number 4 which was flushed with inert gas and the suspension was slowly filtered into a round-bottomed flask. The filtrate was concentrated to about half its volume under reduced pressure, resulting in some of the complex crystallizing. The suspension obtained contained about 200 ml of solvent and theoretically 40 mmol of complex IV.

f) Preparation of Complex I 3.0 g (0.258 mmol) of THF were added to the suspension from step e). 99.7 g (100.1 mmol) of a 7.95% strength by weight solution of acetyl chloride in toluene were subsequently added at room temperature via the dropping funnel. The mixture was stirred at room temperature. After one hour, a yellow precipitate appeared and the reaction mixture was then stirred for a further 60 hours at room temperature. The $^1$H-NMR spectrum of the mixture indicated the formation of the metallocene compound I. The yellow precipitate was filtered off, washed twice with 15 ml of toluene and subsequently dried under reduced pressure. This gave 11.2 g of the target compound I. The $^1$H-NMR spectrum showed the presence of the pure racemate form with only small traces of impurities. Yield: 47% based on ligand used.

| Elemental analysis: | C % (calculated) | 62.48 | C % (found) | 57.7 |
|---|---|---|---|---|
| | H % (calculated) | 4.54 | H % (found) | 5.0 |
| | Cl % (calculated) | 12.29 | Cl % (found) | 15.3 |
| | Zr % (calculated) | 15.82 | Zr % (found) | 15.0 |

EXAMPLE 6

Preparation of rac-dimethylsilylbis(2-methylbenzo[e]indenyl)zirconium dichloride (I) via racemoselective synthesis of dimethylsilylbis(2-methylbenzo[e]indenyl)zirconium bis-(3,5-di-tert-butylphenoxide) (IV) using DME as Lewis base a) Preparation of $ZrCl_4(DME)$ In a dry 500 ml round-bottomed flask which had been flushed with inert gas and was provided with stopcock and magnetic stirrer bar and also a dropping funnel, 10.6 g (45.48 mmol) of $ZrCl_4$ were suspended in 44 g of toluene. The suspension was cooled to about 4° C. in an ice bath. 5.3 g of DME were then slowly added dropwise via the dropping funnel over a period of 15 minutes. The suspension was warmed to room temperature and stirred for one hour.

b) Preparation of $Li(3,5-(t-Bu)_2—C_6H_2O)$

In a dry 250 ml round-bottomed flask which had been flushed with inert gas and was provided with stopcock and magnetic stirrer bar and also a dropping funnel, 18.9 g (91.60 mmol) of 3,5-di-tert-butylphenol were dissolved in 55 g of toluene and 9.2 g of DME. The solution was cooled to about 4° C. in an ice bath. 28.3 g of a 20% strength by weight BuLi solution were subsequently added via the dropping funnel. After the addition was complete, the mixture was allowed to warm to room temperature and was stirred at room temperature for a further 50 minutes.

c) Preparation of $Cl_2Zr(3,5-(t-Bu)_2—C_6H_3O)_2(DME)$

The suspension from step a) was transferred under nitrogen by means of a syringe into the solution from step b) at room temperature over a period of several minutes. The resulting suspension was stirred at room temperature for a further 2.5 hours and subsequently heated to 80° C.

d) Preparation of $Me_2Si(2-Me-benzo[e]ind)_2Li_2$

In a dry 1 000 ml round-bottomed flask which had been flushed with inert gas and was provided with magnetic stirrer bar, dropping funnel and vacuum connection with stopcock, 15.8 g (37.92 mmol) of ligand $Me_2Si(1-H-2-Me-benzo[e]ind)_2$ were suspended in 52 g of toluene and 6.1 g of DME. 26.0 g of a 20% strength by weight BuLi solution were quickly added dropwise to the suspension at room temperature. The mixture was heated to 80° C. and stirred at this temperature for 2.5 hours.

e) Preparation of complex IV

The suspension from step c) was added at 80° C. under nitrogen by means of a syringe to the suspension from step d) over a period of a few minutes. The mixture was slowly cooled to room temperature and stirred at room temperature for a further 60 hours. The $^1$H-NMR spectrum indicated the formation of the complex IV with a rac/meso ratio of about 10:1. The suspension was subsequently filtered through a glass frit number 4 at room temperature. The filter cake was washed three times with 100 g of warm toluene and once with 200 g of toluene having a temperature of 80° C. The filtrate was evaporated to about 150 ml at 40° C. under reduced pressure, resulting in some of the complex crystallizing.

f) Preparation of Complex I 3.4 g of THF were added to the suspension obtained in step e). 7.2 g of acetyl chloride in 200 g of toluene were subsequently added at room temperature via the dropping funnel. The mixture was stirred at room temperature for 12 hours. The reaction mixture was subsequently filtered under inert gas through a glass filter frit number 3. The yellowish precipitate was washed twice with 20 g of toluene and subsequently dried under reduced pressure. This gave 12.2 g of the target compound I. The $^1$H-NMR spectrum showed the formation of the pure rac form of I with only traces of impurities. Yield: 56% based on ligand.

| Elemental analysis: | C % (calculated) | 62.48 | C % (found) | 61.8 |
|---|---|---|---|---|
| | H % (calculated) | 4.54 | H % (found) | 4.8 |
| | Cl % (calculated) | 12.29 | Cl % (found) | 11.9 |
| | Zr % (calculated) | 15.82 | Zr % (found) | 15.5 |

COMPARATIVE EXAMPLE A

Preparation of rac-dimethylsilylbis(2-methylbenzo[e]indenyl)zirconium dichloride (I) via racemoselective synthesis of dimethylsilylbis(2-methylbenzo[e]indenyl)zirconium bis-(3,5-di-methylphenoxide) (IV) using THF as Lewis base a) Preparation of $ZrCl_4(THF)_2$ In a dried, inerted 500 ml three neck round flask equipped with a magnetical stirrbar, a dropping funnel and suction device with valve 10.6 g of $ZrCl_4$ were suspended in 50 g of toluene. The suspension was cooled to approximately 4° C. and drop by drop 6.6 g of THF were slowly added during 15 minutes by a dropping funnel. The white suspension was allowed to come to room temperature and was further stirred for 1 h.

b) Preparation of $Li(3,5-Me_2—C_6H_2O)$

In a dried, inerted 250 ml three neck round flask equipped with a magnetical stirrbar, a dropping funnel and suction device with valve 11.2 g of 3,5-di-methyl-phenol were solved in 50 g of toluene and 6.6 g of THF. The red solution was cooled to approximately 4° C. and 29 g of a BuLi-solution were added by a dropping funnel. A blue suspension was formed. After the addition was completed, the white suspension was allowed to come to room temperature and was further stirred for 1 h at room temperature.

c) Preparation of $Cl_2Zr(3,5-Me_2—C_6H_3O)_2(THF)_2$

The suspension from reactionstep b) was transferred under nitrogen via a canula into the suspension of reactionstep a) at room temperature and within several minutes. Remaining rests of Lithiumphenolate were washed with 10 g of toluene. The brown suspension was further stirred for 2.5 hours at room temperature.

d) Preparation of $Me_2Si(2-Me-benz[e]ind)_2Li_2$

In a dried, inerted 1000 ml three neck round flask equipped with a magnetical stirbar, a dropping funnel and suction device with valve 15.9 g of the ligand $Me_2Si(1-H-2-Me-benz[e]ind)_2$ were suspended in 50 g of toluene and 3.9 g of THF. 25.6 g of a BuLi solution were dropped to into the suspension at room temperature. The yellow suspension was heated to 80° C. and was further stirred for 1.5 hours at this temperature.

e) Preparation of $Me_2Si(2-Me-benz[e]ind)_2Zr(3,5-Me_2—C_6H_3O)_2$ and conversion to $Me_2Si(2-Me-benz[e]ind)_2ZrCl_2$ The suspension yielded in rectionstep c) was transferred via a canula under nitrogen into the suspension of reactionstep d) both at 80° C. The reaction mixture turned into a yellow-colored suspension. Remaining rests of $Cl_2Zr(3,5-Me_2—C_6H_3O)_2(THF)_2$ were washed with 10 g of toluene. The suspension was stirred for 2 h at 80° C. 250 g of toluene were added. The suspension was transferred at 80° C. into an inertgas protected glas-filter frit No. 4 under nitrogen via a canula. The suspension was filtered (slow filtration) into a roundflask with valve. The filtercake was washed with 50 g of toluene. The filtrate was strongly concentrated under reduced pressure (80% of the solvents were evaporated) and then left at room temperature. At room temperature, 7.3 g of acetylchloride were added via a syringe and the reaction mixture was stirred for 12 h at room temperature. The yellow precipitate was filtered and dried under vaccuo. 5.2 g of $Me_2Si(2-Me-benz[e]ind)_2ZrCl_2$ in pure rac form were obtained. Yield: 24% based on the amount of indenyl ligand used.

EXAMPLE 7

Preparation of rac-dimethylsilylbis(2-methylbenzo[e]indenyl)zirconium dichloride (I) in a single-vessel reaction a) Preparation of $Me_2Si(2-Me-benzo[e]ind)_2Li_2$ 22.5 g of a 60% strength solution (in toluene) of 2-Me-benzindene (74.90 mmol) were placed in a dry 1 000 ml round-bottomed flask which had been flushed with inert gas and was provided with a stopcock. 290 g of toluene and 8.3 g of THF were additionally added. At room temperature, 25.7 g of a 20% strength by weight solution of BuLi in toluene were added via a dropping funnel while stirring. The reaction mixture was subsequently stirred at 60° C. for one hour and then cooled to room temperature. 5.0 g of $Me_2SiCl_2$ were then added via the dropping funnel. After the addition was complete, the reaction mixture was heated to 80° C. and stirred at this temperature for 1.5 hours. The mixture was subsequently allowed to cool to room temperature and 25.7 g of a 20% strength BuLi solution in toluene were added. After the addition was complete, the reaction mixture was heated to 80° C. and stirred at this temperature for a further 2 hours. It was then allowed to cool to room temperature.

b) Preparation of $ZrCl_4(THF)_2$

In a 500 ml round-bottomed flask with stopcock, 10.5 g of $ZrCl_4$ were suspended in 50 g of toluene. The suspension was cooled to about 4° C. in an ice bath and 8.0 g of THF were then added slowly via a dropping funnel. The resulting suspension was allowed to warm to room temperature while stirring.

c) Preparation of $Li(3,5-(t-Bu)_2—C_6H_2O)$

In a 1 000 ml round-bottomed flask with stopcock, 18.9 g of 3,5-di-tert-butylphenol (91.60 mmol) were dissolved in 50 g of toluene and 8 g of THF. The solution was cooled in an ice bath and 29 g of a 20% strength by weight BuLi solution in toluene were then added slowly. The reaction mixture was allowed to warm to room temperature while stirring.

d) Preparation of $Cl_2Zr(3,5-(t-Bu)_2—C_6H_3O)_2(THF)_2$

The suspension from step c) was added under nitrogen by means of a syringe to the suspension from step b) at room temperature and the mixture was stirred at room temperature.

e) Preparation of Complex IV

The suspension from step d) was added at room temperature to the suspension from step a). The mixture was subsequently stirred at room temperature for 12 hours. The $^1$H-NMR spectrum of the reaction mixture indicated a rac/meso ratio of about 11:1. The mixture was stirred at 80° C. for 40 minutes and subsequently filtered under nitrogen through a glass filter frit. The round-bottomed flask was rinsed out using 20 ml of toluene, and the filter cake was washed twice with 20 ml of toluene. The $^1$H-NMR spectrum of the filtrate indicated a rac/meso ratio of about 9:1. The filtrate had a mass of 614.6 g and was evaporated to 123.5 g at 40° C. under reduced pressure. The theoretical concentration of IV is 20%.

f) Preparation of rac-dimethylsilylbis(2-methylbenzo[e]indenyl)zirconium dichloride (I)

At room temperature, 8.9 g of acetyl chloride in 25 g of toluene were slowly added dropwise to the concentrated filtrate from step e) via a dropping funnel. After the addition was complete, the mixture was stirred at room temperature for a further 12 hours. A precipitate formed during this time. A further 100 ml of toluene were added to this suspension and the mixture was stirred for another 2 hours. The resulting suspension was filtered, and the round-bottomed flask was rinsed out using 20 ml of toluene. The filter cake was washed twice with 20 ml of toluene and subsequently dried under reduced pressure. This gave 9.3 g of the target compound I in pure rac form with slight traces of impurities.

Yield: 43% based on the amount of indenyl ligand used.

What is claimed is:

1. A process for the diastereoselective synthesis of rac-diorganosilylbis(2-methylbenzo[e]indenyl)zirconium compounds of the formula I,

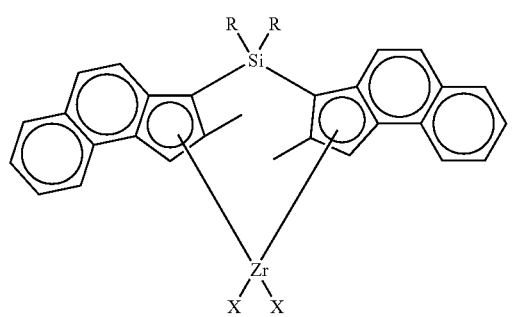

which comprises the following steps:
a) reaction of a compound of the formula II with a zirconium bisphenoxide complex of the formula III to form the ansa-zirconocene bisphenoxide complex of the formula IV,

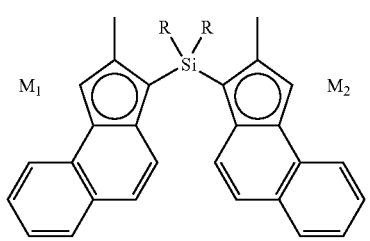

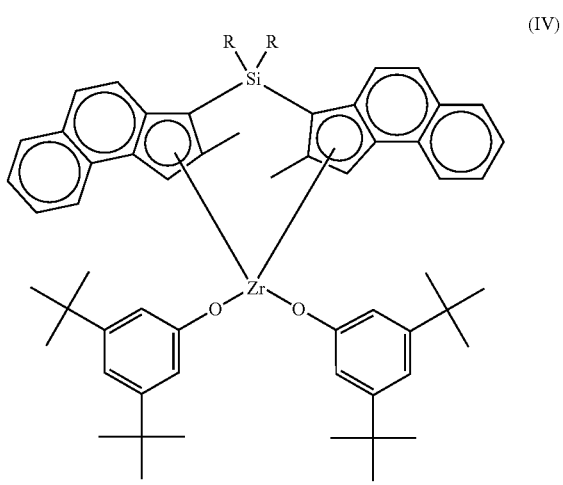

b) replacement of the phenoxide groups of IV by X using suitable replacement reagents to give the compound of the formula I;

where
the substituents X can be identical or different and are each F, Cl, Br, I, or linear, cyclic or branched $C_{1-10}$-alkyl; and the substituents R can be identical or different and are each linear, cyclic or branched $C_{1-10}$-alkyl or $C_{6-10}$-aryl; and LB is a suitable Lewis base, and $M_1$ and $M_2$ are monovalent positive alkali metal ions or $M_1$ and $M_2$ together represent a divalent positive alkaline earth metal ion.

2. A process as claimed in claim 1 for the diastereoselective synthesis of rac-diorganosilylbis(2-methylbenzo[e]indenyl)zirconium compounds of the formula I,

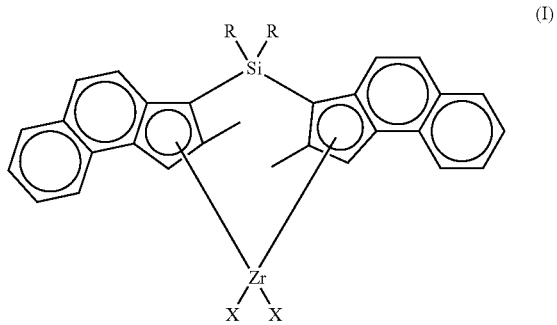

which comprises the following steps:
a) deprotonation of 2-methylbenzo[e]indene by means of a suitable deprotonating agent;
b) reaction of the deprotonated 2-methylbenzo[e]indene with a diorganosilyl compound $R_2SiY_2$, where the substituents R can be identical or different and are each linear, cyclic or branched $C_{1-10}$-alkyl or $C_{6-10}$-aryl and the leaving groups Y can be identical or different and are each F, Cl, Br or I, and subsequent repeat deprotonation by means of a suitable deprotonating agent, giving a compound of the formula II:

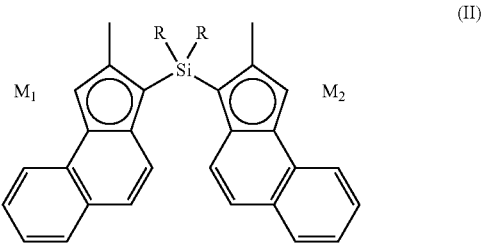

(II)

where $M_1$ and $M_2$ are monovalent positive alkali metal ions or $M_1$ and $M_2$ together represent a divalent positive alkaline earth metal ion;
c) reaction of the compound of the formula II with a zirconium bisphenoxide complex of the formula III:

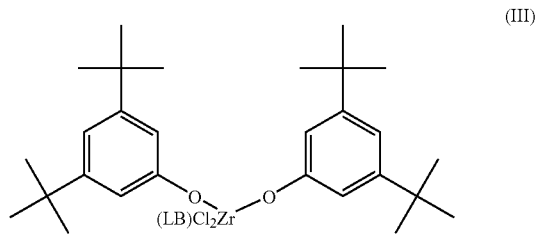

(III)

where LB is a suitable Lewis base, to give a compound of the formula IV:

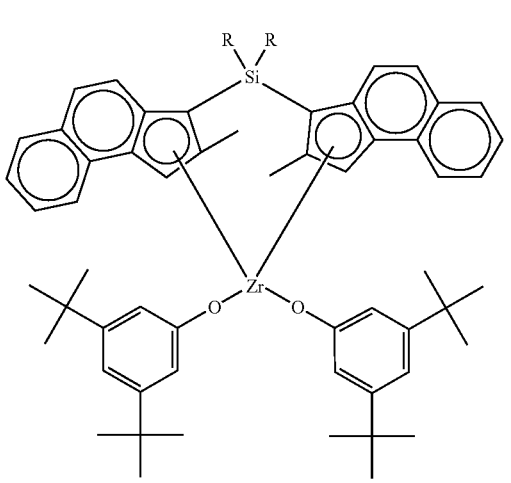

(IV)

d) reaction of the compound of the formula IV with suitable replacement reagents so as to replace the phenoxide groups of IV by X to give the compound of the formula I, where the substituents X can be identical or different and are each F, Cl, Br, I or linear, cyclic or branched $C_{1-10}$-alkyl.

3. A process as claimed in claim 2, wherein the deprotonating agent is selected from among n-butyllithium, tert-butyllithium, sodium hydride, potassium tert-butoxide, Grignard reagents of magnesium, magnesium compounds, alkaline earth metal alkyl compounds or alkali metal alkyl compounds.

4. A process as claimed in claim 2 carried out without isolation of intermediates after individual process steps.

5. A process as claimed in claim 1, wherein the replacement reagent used is an aliphatic or aromatic carboxylic acid halide optionally in a solvent.

6. A process as claimed in claim 1, wherein the replacement reagent used is $SOCl_2$, silicon tetrachloride, methylaluminum dichloride, dimethylaluminum chloride, aluminum trichloride or ethylaluminum dichloride.

7. A process as claimed in claim 1, wherein the replacement reagent used is HF, HBr, HI, or HCl, optionally as a solution in water or organic solvent.

8. A process as claimed in claim 1, wherein the replacement reagent used is an organoaluminum compound.

9. A process as claimed in claim 1, wherein the reaction is carried out in Lewis base-containing solvent mixtures of hydrocarbons and ethers or amines or both.

10. A process as claimed in claim 9, wherein the Lewis base is present in an amount of 0.01–50 mol %, based on the solvent mixture.

11. A process as claimed in claim 1, wherein LB in the formula III is tetrahydrofuran (THF), dimethoxyethane (DME) or tetramethylethanediamine (TMEDA).

12. A process as claimed in claim 1, wherein $M_1$ and $M_2$ are lithium, sodium, potassium, rubidium or cesium ions or together represent magnesium.

13. A process as claimed in claim 1, wherein the substituents R are methyl, ethyl, n-propyl, isopropyl, n-butyl, isobutyl, phenyl or combinations thereof.

14. A process as claimed in claim 1 wherein the substituents X are F, Cl, Br, I, methyl, ethyl, n-propyl, isopropyl, n-butyl or isobutyl.

15. A process as claimed in claim 1, wherein R is methyl or ethyl, X is Cl and LB is THF or DME.

16. A racemic transition metal compound of the formula IV:

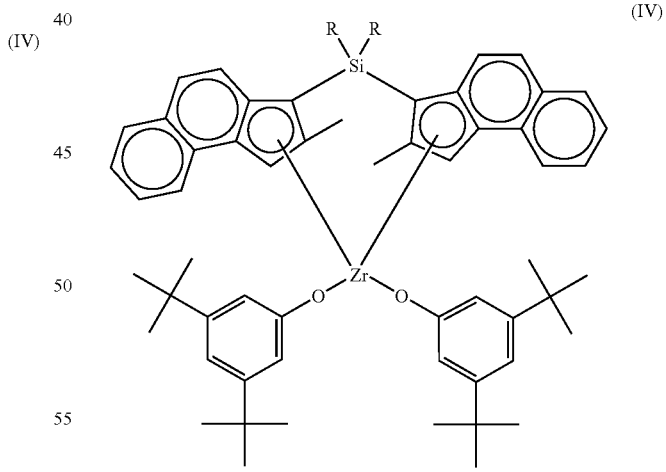

(IV)

where the substituents R may be identical or different and are each linear, cyclic or branched $C_{1-10}$-alkyl or $C_{6-10}$-aryl.

17. A compound as claimed in claim 16, wherein the substituents R are methyl, ethyl, n-propyl, isopropyl, n-butyl, isobutyl phenyl or combinations thereof.

18. A catalyst which comprises the racemic compound as claimed in claim 16.

* * * * *

UNITED STATES PATENT AND TRADEMARK OFFICE
CERTIFICATE OF CORRECTION

PATENT NO. : 7,098,354 B2
APPLICATION NO. : 10/532511
DATED : August 29, 2006
INVENTOR(S) : Hans-Robert-Hellmuth Damrau et al.

It is certified that error appears in the above-identified patent and that said Letters Patent is hereby corrected as shown below:

In the Claims:

In Claim 17, column 20, line 63, "tyl, isobutyl phenyl or combinations thereof." should read -- tyl, isobutyl, phenyl or combinations thereof. --

Signed and Sealed this

Thirtieth Day of January, 2007

JON W. DUDAS
*Director of the United States Patent and Trademark Office*